US00PP18557P2

(12) United States Plant Patent
Korlipara

(10) Patent No.: US PP18,557 P2
(45) Date of Patent: Mar. 4, 2008

(54) ***HEUCHERA* PLANT NAMED 'RASPBERRY RIPPLE'**

(50) Latin Name: ***Heuchera* hybrid**
Varietal Denomination: Raspberry Ripple

(75) Inventor: Harini Korlipara, Canby, OR (US)

(73) Assignees: Terra Nova Nurseries, Inc., Canby, OR (US); The Behnke Nurseries Co., Beltsville, MD (US)

( * ) Notice: Subject to any disclaimer, the term of this patent is extended or adjusted under 35 U.S.C. 154(b) by 11 days.

(21) Appl. No.: 11/592,047

(22) Filed: Nov. 1, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Wendy Haas
(74) *Attorney, Agent, or Firm*—Klarquist Sparkman, LLP

(57) ABSTRACT

A new and distinct hybrid of *Heuchera* plant characterized by strong pink variegation on an almost black leaf. In summer the color on the older leaves lightens to cream and pink.

1 Drawing Sheet

Botanical classification: *Heuchera* hybrid.
Variety denomination: 'Raspberry Ripple'.

The present invention relates to a new and distinct cultivar of *Heuchera* hybrid and given the cultivar name of 'Raspberry Ripple'. *Heuchera* is in the family Saxifragaceae. *Heuchera* 'Raspberry Ripple' originated as a tissue culture mutation of *Heuchera* 'Midnight Rose'. It was found in the Canby tissue culture lab and was brought out and evaluated for uniformity.

This new and unique *Heuchera* is distinguished by:

1. Strong pink variegation on an almost black leaf.
2. In summer the strong pink color lightens to cream and pink on the older leaves.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg. shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
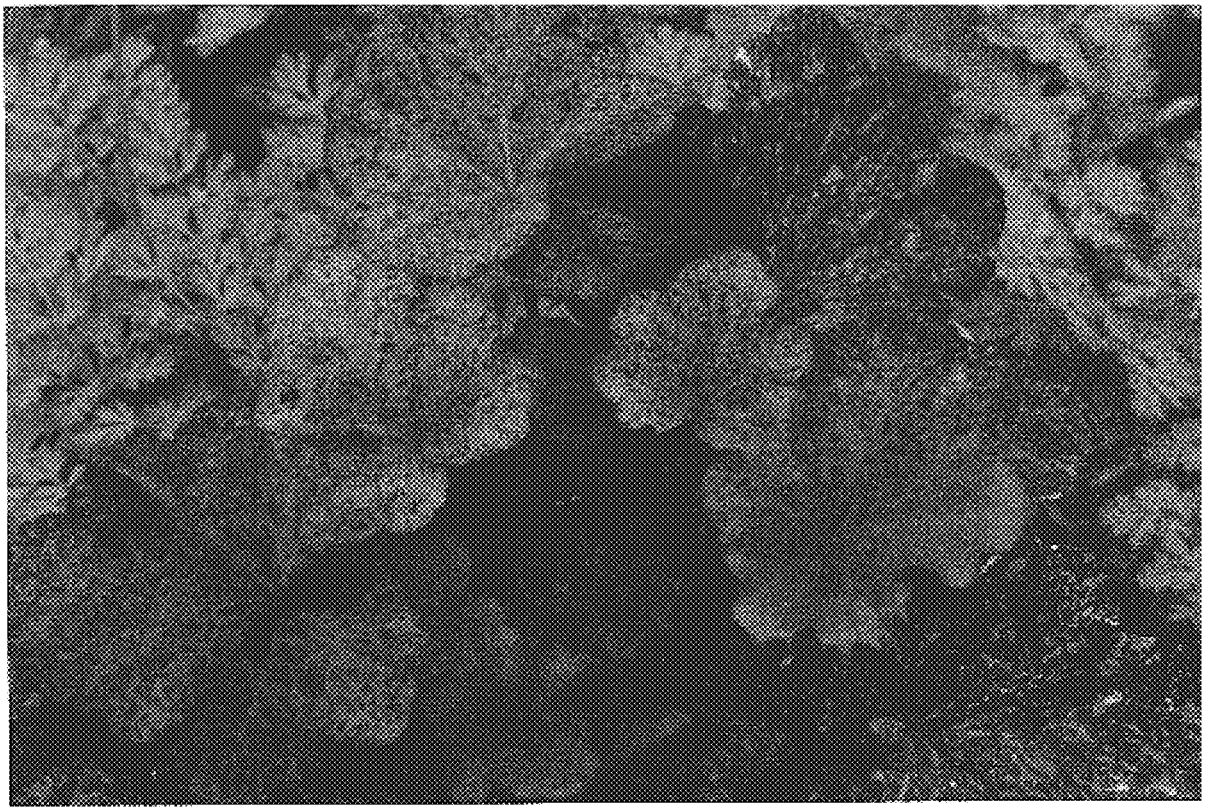
FIG. 1 shows a 9 month old *Heuchera* 'Raspberry Ripple' growing in a one gallon container in a cool greenhouse in Canby, Oreg.

The following is a detailed description of the new *Heuchera* cultivar based on observations taken in September of a nine-month-old specimen grown a one gallon container in an open air shade house with 50% shade cover and added irrigation in the summer months in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:
- *Form.*—Basal rosette, herbaceous perennial.
- *Hardiness.*—USDA Zone 4 to 9.
- *Size.*—30 cm tall from the ground to the top of the foliage and 35 cm wide.
- *Habit.*—Mounding.
- *Vigor.*—Excellent.
- *Roots.*—Fibrous, freely branching, fine, and white in color, roots develop easily from cuttings.

Leaf:
- *Type.*—Simple.
- *Arrangement.*—Rosette.
- *Shape.*—Orbicular to slightly ovate, cupping upward when plants are mature.
- *Lobing/division.*—7 rounded lobes, with 2 shallow secondary lobes on the terminal and longest lobe and 1 shallow secondary lobe on the lateral lobes.
- *Venation.*—Palmate.
- *Margins.*—Broadly crenate.
- *Apex.*—Mucronulate to obtuse.
- *Base.*—Cordate, lobes strongly overlapping.
- *Blade size.*—Grows to 9.5 cm long and 8.5 cm wide.
- *Surface texture.*—Sparsely puberulous on both sides.
- *Petiole length.*—Grows to 22 cm.
- *Petiole texture.*—Glandular puberulent.
- *Petiole color.*—Greyed Orange 177A and Greyed Purple 183A.
- *Leaf color.*—Topside — in spring pink, Greyed Purple 186B, with blotches of Black 202A; in summer the pink in older leaves lightens to Red 36A, Greyed Purple 186D, and Greyed Red 182D with the blotches lightning to Brown 200A. Bottom side — between Greyed Purple 186C and Red Purple 72B with dark areas closest to Greyed Purple 187A, but duller.

Inflorescence:
- *Type.*—Thyrse.
- *Number of flowers.*—About 100 per thyrse.

*Peduncle description.*—Unbranched, with 2 or 3 petiolate bracts per scape, bracts grow to 5 cm long and 4 cm wide, ovate, serrate, with 3 main lobes, peduncle grows to 74 cm tall and 5 mm wide, glandular puberulent, Greyed Purple 187A.

*Pedicel description.*—6 mm long and 1 mm wide, glandular puberulent, Greyed Purple 187A.

*Bloom period.*—May to July in Canby, Oreg.

Flower bud:

*Size.*—4 mm long, 2 mm wide.

*Description.*—Glandular puberulent, ovoid.

*Color.*—Greyed Purple 186A with Greyed Yellow 160A at tip.

Flower:

*Type.*—Perfect, zygomorphic.

*Shape.*—Campanulate.

*Size.*—6 mm long and 5 mm wide.

*Petal description.*—5, inconspicuous, 3 mm long and 1 mm wide, elliptic with a clawed base, entire, acute, White 155D and glandular on both sides.

*Calyx description.*—4 mm deep and 3 mm wide, urceolate, with 5 lobes divided ½ way to the base, broadly oblong with glandular hairs on both sides, entire, acute, Yellow Green 152A inside and on lobes inside and out, outside tube of calyx Brown 200A.

*Stamen.*—5, about 2 mm long, filaments Yellow White 158C, 1.2 mm long, anthers sterile, 0.8 mm long, Greyed Yellow 160D, no pollen.

*Pistil.*—4 mm long, Yellow Green 145A overall, ovary 2 mm long and 2 beaked style 2 mm long.

*Fragrance.*—None.

*Lastingness.*—Each thyrse blooms for about 2 weeks on the plant.

Fruit:

*Type.*—Two-beaked ovoid capsule.

*Fertility.*—Low.

*Color.*—Tan. RHS 160C Greyed-Yellow to 199C Grey-Brown.

Seed:

*Shape.*—Linear.

*Size.*—2 mm. long.

*Color.*—Black RHS 202A.

Disease and pest tolerance: Excellent disease resistance to powdery mildew, the common problem of *Heuchera.* Susceptible to root weevils. Not highly susceptible to *Heuchera* rust.

COMPARISON TO SIMILAR *HEUCHERA*

Compared to *Heuchera* 'Midnight Rose' (U.S. Plant Patent applied for), the mother plant, this new cultivar is the same except for much stronger pink variegation.

I claim:

1. A new and distinct hybrid of *Heuchera* plant substantially as shown and described.

* * * * *